US00PP32763P2

(12) United States Plant Patent
Koot

(10) Patent No.: US PP32,763 P2
(45) Date of Patent: Jan. 19, 2021

(54) ***VERBENA* PLANT NAMED 'DOVERBVOOBURGSTA'**

(50) Latin Name: ***Verbena* x *hybrida***
Varietal Denomination: Doverbvooburgsta

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/873,194

(22) Filed: Feb. 25, 2020

(51) Int. Cl.
*A01H 5/02* (2018.01)
*A01H 6/86* (2018.01)

(52) U.S. Cl.
USPC ..... Plt./308
CPC ..... *A01H 6/86* (2018.05)

(58) Field of Classification Search
USPC ..... Plt./308
CPC ..... A01H 6/86; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Verbena* plant named 'Doverbvooburgsta', characterized by its mounding to semi-trailing plant habit; moderately vigorous growth habit; freely branching habit; early and freely flowering habit; large star-patterned red purple and light pink bi-colored flowers; and good garden performance.

1 Drawing Sheet

Botanical designation: *Verbena* x *hybrida*.
Cultivar denomination: 'DOVERBVOOBURGSTA'.

BACKGROUND OF THE INVENTION

The present invention relates to a new and distinct cultivar of *Verbena* plant, botanically known as *Verbena* x *hybrida* and hereinafter referred to by the name 'Doverbvooburgsta'.

The new *Verbena* plant is a product of a planned breeding program conducted by the Inventor in Rheinberg, Germany. The objective of the breeding program is to create new vigorous and early-flowering *Verbena* plants with numerous large and attractive flowers.

The new *Verbena* plant is a naturally-occurring whole plant mutation of a proprietary selection of *Verbena* x *hybrida* identified as code number VV02-001928-001, not patented. The new *Verbena* plant was discovered and selected by the Inventor as a single flowering plant within a population of plants of the mutation parent selection in a controlled greenhouse environment in Rheinberg, Germany in May, 2018.

Asexual reproduction of the new *Verbena* plant by terminal vegetative cuttings in a controlled greenhouse environment in Rheinberg, Germany since June, 2018 has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Doverbvooburgsta'. These characteristics in combination distinguish 'Doverbvooburgsta' as a new and distinct *Verbena* plant:

1. Mounding to semi-trailing plant habit.
2. Moderately vigorous growth habit.
3. Freely branching habit.
4. Early and freely flowering habit.
5. Large star-patterned red purple and light pink bi-colored flowers.
6. Good garden performance.

Plants of the new *Verbena* differ primarily from plants of the mutation parent selection in flower color as plants of the new *Verbena* have red purple and light pink bi-colored flowers whereas plants of the mutation parent selection have red and white bi-colored flowers.

Plants of the new *Verbena* can be compared to plants of the *Verbena* x *hybrida* 'Empress Flair Burgundy', not patented. In side-by-side comparisons, plants of the new *Verbena* differ primarily from plants of 'Empress Flair Burgundy' in flower color as plants of the new *Verbena* have red purple and light pink bi-colored flowers whereas plants of 'Empress Flair Burgundy' have solid red purple-colored flowers. In addition, plants of the new *Verbena* have thicker lateral branches than plants of 'Empress Flair Burgundy'.

BRIEF DESCRIPTION OF THE PHOTOGRAPH

The accompanying colored photograph illustrates the overall appearance of the new *Verbena* plant showing the colors as true as it is reasonably possible to obtain in colored reproductions of this type. Colors in the photograph may differ slightly from the color values cited in the detailed botanical description which accurately describe the colors of the new *Verbena* plant. The photograph (FIG. 1) is a top perspective view of a typical flowering plant of 'Doverbvooburgsta'.

DETAILED BOTANICAL DESCRIPTION

The aforementioned photograph and following observations, measurements and values describe plants grown in 13-cm containers during the spring in a glass-covered greenhouse in Rheinberg, Germany and under cultural practices typical of commercial *Verbena* production. During the production of the plants, day and night temperatures averaged 18° C. and light levels averaged 1,500 lux. Plants were pinched one time three weeks after planting and were twelve weeks old when the photographs and the description were taken. In the description, color references are made to The Royal Horticultural Society Colour Chart, Fifth Edition, except where general terms of ordinary dictionary significance are used.

Botanical classification: *Verbena* X *hybrida* 'Doverbvooburgsta'.

Parentage: Naturally-occurring whole plant mutation of a proprietary selection of *Verbena* x *hybrida* identified as code number VV02-001928-001, not patented.

Propagation:

*Type*.—Terminal vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; close to 158A in color, actual color of the roots is dependent on substrate composition, water quality, fertilizers, substrate temperature and age of roots.

*Rooting habit*.—Freely branching; dense.

Plant description:

*Plant habit*.—Mounding to semi-trailing plant habit; freely branching habit with about six primary lateral branches each with about six to eight secondary lateral branches; pinching enhances lateral branch development; dense and bushy plant habit; moderately vigorous growth habit; moderate growth rate.

*Plant height, soil level to top of foliar plane*.—About 20 cm.

*Plant height, soil level to top of floral plane*.—About 20 cm.

*Plant diameter*.—About 20 cm.

Lateral branch description:

*Length*.—About 20 cm.

*Diameter*.—About 3.8 mm.

*Internode length*.—About 5.5 cm.

*Strength*.—Strong.

*Texture and luster*.—Pubescent; semi-glossy.

*Color, developing*.—Close to 145A.

*Color, developed*.—Close to 144A; at the internodes, close to 143B.

Leaf description:

*Arrangement*.—Opposite, simple.

*Length*.—About 4 cm.

*Width*.—About 2 cm.

*Shape*.—Lanceolate.

*Apex*.—Acute.

*Base*.—Attenuate.

*Margin*.—Lobed; sinuses medium in depth and divergent.

*Texture and luster, upper surface*.—Pubescent, coarse; semi-glossy.

*Texture and luster, lower surface*.—Pubescent, coarse; matte.

*Venation pattern*.—Pinnate.

*Color*.—Developing leaves, upper surface: Close to 141B. Developing leaves, lower surface: Close to 143A. Fully expanded leaves, upper surface: Close to 139A; venation, close to 139C. Fully expanded leaves, lower surface: Close to 139B; venation, close to 138C.

*Petioles*.—Length: About 5 mm. Diameter: About 1.8 mm. Strength: Moderately strong. Texture and luster, upper and lower surfaces: Smooth, glabrous; matte. Color, upper surface: Close to 142B. Color, lower surface: Close to 142C.

Flower description:

*Flower arrangement and habit*.—Salverform flowers arranged in hemispherical terminal umbels; umbels dense and mounding; numerous umbels per plant; flowers face upward or outwardly depending on position in the umbel; freely flowering habit with about twelve flowers per inflorescence and numerous inflorescences per plant.

*Fragrance*.—None detected.

*Natural flowering season*.—Plants flower continuously from the spring through the fall in Germany; plants begin flowering about eight weeks after planting.

*Flower longevity*.—Individual flowers last about one week on the plant; flowers persistent.

*Inflorescence height*.—About 3.2 cm.

*Inflorescence diameter*.—About 6.5 cm.

*Flower buds*.—Length: About 1.3 cm. Diameter: About 4 mm. Shape: Oval to tubular. Texture and luster: Rippled; matte. Color: Close to 143B.

*Flowers*.—Appearance: Salverform, five-parted fused corolla. Diameter: About 2.3 cm. Depth: About 2.6 cm. Throat diameter: About 1.5 mm. Tube length: About 2.1 cm. Tube diameter: About 1 mm.

*Corolla*.—Arrangement: Single whorl of five fused petals. Petal lobe length: About 3.2 cm. Petal lobe width: About 1 cm. Petal lobe shape: Obovate. Petal lobe apex: Emarginate. Petal margin: Entire. Petal texture and luster, upper and lower surfaces: Smooth, glabrous; matte. Throat texture and luster: Smooth, glabrous; matte. Tube texture and luster: Smooth, glabrous; matte. Color: Petal lobe, when opening, upper surface: Star-shaped bi-colored pattern, close to 59A to 59B and 56D. Petal lobe, when opening, lower surface: Star-shaped bi-colored pattern, close to 64A and 155D. Petal lobe, fully opened, upper surface: Star-shaped bi-colored pattern, close to 59A and 55D; venation, similar to lamina; colors becoming closer to 93A and 55D with development. Petal lobe, fully opened, lower surface: Star-shaped bi-colored pattern, close to 59B and 56D; venation, similar to lamina; colors becoming closer to 90A and 56D with development. Throat: Close to 142D; venation, close to 142D. Tube: Close to 142D; venation, close to 142D.

*Calyx*.—Arrangement: Tubular calyx with five fused sepals. Length: About 1.4 cm. Diameter: About 2.2 mm. Sepal length: About 1.2 cm. Sepal width: About 1 mm. Sepal shape: Ligulate. Sepal apex: Acute. Sepal margin: Entire. Sepal texture and luster, upper surface: Pubescent, coarse; semi-glossy. Sepal texture and luster, lower surface: Pubescent, coarse; matte. Sepal color, upper and lower surfaces: Close to 144A and 145A.

*Peduncles*.—Length: About 5 cm. Diameter: About 2 mm. Strength: Strong. Aspect: Mostly upright. Texture and luster: Pubescent; semi-glossy. Color: Close to 145A.

*Pedicels*.—Length: About 0.5 mm. Diameter: About 0.5 mm. Strength: Strong. Aspect: Mostly upright. Texture and luster: Smooth, glabrous; semi-glossy. Color: Close to 145A.

*Reproductive organs*.—Stamens: Quantity and arrangement: About four to five per flower, adnate to corolla tube. Filament length: About 1 mm. Filament color: Close to 155C. Anther length: About 0.9 mm. Anther shape: Oval. Anther color: Close to 150B. Pollen amount: Moderate. Pollen color: Close to 2C. Pistils: Quantity: One per flower. Pistil length: About 2.1 cm. Style length: About 1.7 cm. Style color: Close to 144D. Stigma diameter: About 1 mm. Stigma shape: Bi-parted; fimbriate. Stigma color: Close to 143A. Ovary color: Close to 144C. Fruits: Quantity produced per plant: About 50 during the flowering season. Length: About 5 mm. Diameter: About 1 mm. Texture: Rough. Color: Close to 199C. Seeds: Quantity per flower: About four. Length: About 4.8 mm. Diameter: About 0.8 mm. Texture: Smooth, glabrous. Color: Close to 199B.

Garden performance: Plants of the new *Verbena* have been observed to have good garden performance and to be suitable for USDA Hardiness Zone 11.

Pathogen & pest resistance: To date, plants of the new *Verbena* have not been observed to be resistant to pathogens and pests common to *Verbena* plants.

It is claimed:

1. A new and distinct *Verbena* plant named 'Doverbvooburgsta' as illustrated and described.

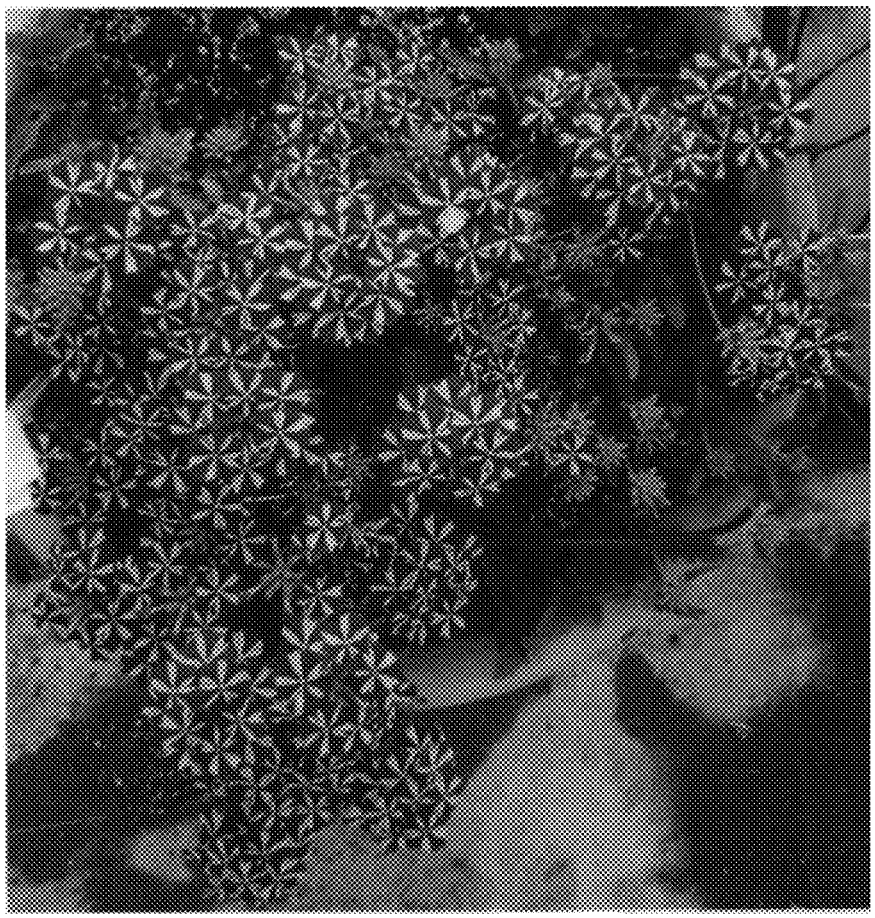

* * * * *